United States Patent
Beck

(10) Patent No.: US 8,835,887 B2
(45) Date of Patent: Sep. 16, 2014

(54) RADIATION SHIELD WITH DISPOSABLE STERILE DRAPE FOR PROTECTING THE HANDS AND ARMS DURING INTERVENTIONAL CARDIOVASCULAR FLUOROSCOPY

(71) Applicant: Thomas J. Beck, Cantonsville, MD (US)

(72) Inventor: Thomas J. Beck, Cantonsville, MD (US)

(73) Assignee: Bar-Ray Products, Inc., Littlestown, PA (US)

( * ) Notice: Subject to any disclaimer, the term of this patent is extended or adjusted under 35 U.S.C. 154(b) by 0 days.

(21) Appl. No.: 13/841,625

(22) Filed: Mar. 15, 2013

(65) Prior Publication Data
US 2013/0320246 A1   Dec. 5, 2013

Related U.S. Application Data

(60) Provisional application No. 61/655,324, filed on Jun. 4, 2012.

(51) Int. Cl.
  G21F 3/00   (2006.01)
  G21F 3/02   (2006.01)
  F16M 11/42  (2006.01)
  A61N 5/00   (2006.01)
  A61M 25/00  (2006.01)

(52) U.S. Cl.
  CPC .. *G21F 3/00* (2013.01); *A61N 5/00* (2013.01); *A61M 25/00* (2013.01)
  USPC ................ 250/515.1; 250/516.1; 250/519.1; 250/505.1

(58) Field of Classification Search
  CPC ....... B29K 2083/00; H05K 7/20; H05K 5/00; H05K 5/0213; G21F 3/00; A61N 5/00
  USPC ...................... 250/515.1, 516.1, 519.1, 505.1
  See application file for complete search history.

(56) References Cited

U.S. PATENT DOCUMENTS

| | | | |
|---|---|---|---|
| 4,581,538 A | 4/1986 | Lenhart | |
| 5,185,778 A | 2/1993 | Magram | |
| 5,417,225 A | 5/1995 | Rubenstein et al. | |
| 6,898,810 B2 | 5/2005 | Steven | |
| 8,674,330 B2 * | 3/2014 | Beck | 250/516.1 |
| 2006/0251203 A1 * | 11/2006 | Okamura et al. | 376/287 |
| 2009/0114857 A1 * | 5/2009 | DeMeo et al. | 250/516.1 |
| 2011/0163248 A1 | 7/2011 | Beck | |
| 2012/0132217 A1 | 5/2012 | Rees | |
| 2012/0248346 A1 * | 10/2012 | Chowdhary et al. | 250/516.1 |

* cited by examiner

*Primary Examiner* — Nikita Wells
(74) *Attorney, Agent, or Firm* — Barry G. Magidoff; Paul J. Sutton

(57) ABSTRACT

A radiation blocking shied for the hands of a clinical operator of fluoroscopic equipment during extended surgery or diagnostic testing.

9 Claims, 5 Drawing Sheets

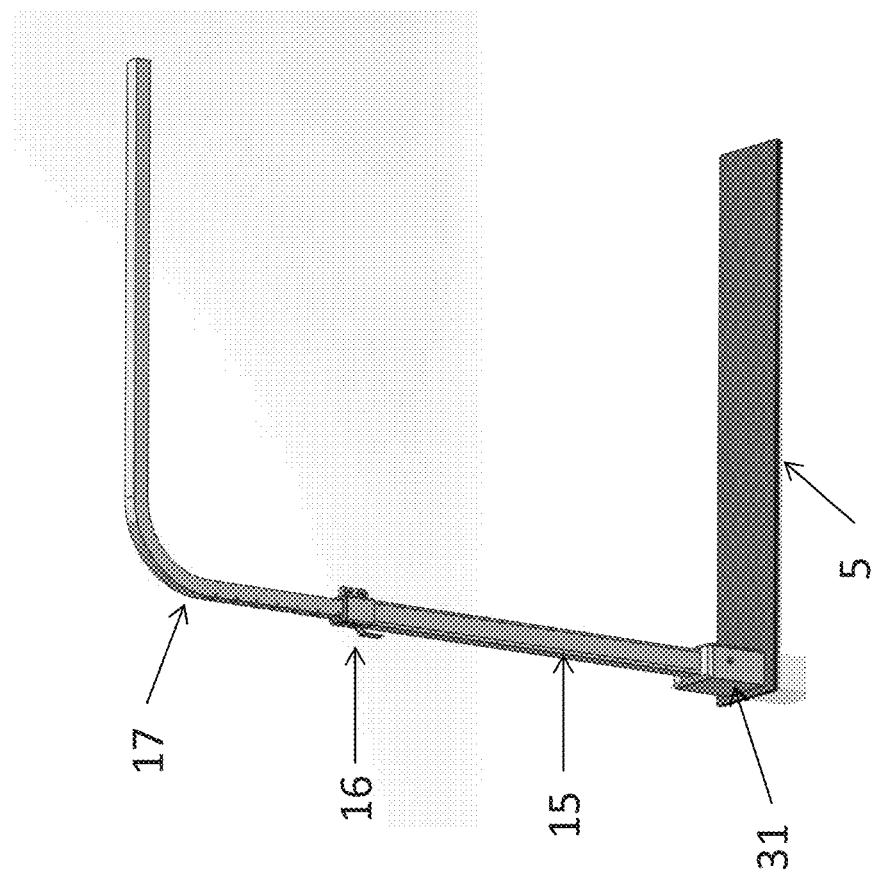

RADIATION SHIELD WITH DISPOSABLE STERILE DRAPE FOR PROTECTING THE HANDS AND ARMS DURING INTERVENTIONAL CARDIOVASCULAR FLUOROSCOPY

This application claims the benefit and filing priority of U.S. Provisional Application No. 61/655,324 filed on Jun. 4, 2012.

FIELD OF THE INVENTION

This invention relates to the field of medical fluoroscopy where a large variety of cardiovascular diagnostic and interventional procedures are accomplished with fluoroscopically guided intravascular catheters and related implements. The invention describes a simple device for more effective shielding of the hands of the medical fluoroscopist from scattered radiation emitted from the body of the patient undergoing the procedure.

BACKGROUND OF THE INVENTION

Catheterization procedures guided by x-ray fluoroscopy are widely done in medicine for diagnostic and therapeutic interventional purposes. The fluoroscopist who is manipulating the catheter for the procedure must be shielded from excessive radiation exposure. Most of the radiation that reaches the fluoroscopist is scattered from the volume of the patient's tissues that are in the direct path of the imaging x-ray beam, which usually is projected from a source usually located beneath the platform upon which the patent is supported. Shielding is typically done by the use of shielding garments worn by the fluoroscopist, including a protective apron to shield the trunk of the body, possibly supplemented with a thyroid shield around the neck, lead glasses etc. The intensity of scattered radiation is greatest at points on the patient that are near the irradiated field margins. The fluoroscopist's hands are in contact with the patient during manipulation of the catheters and typically receive the highest radiation exposure. Because the hands are working within a sterile field any solution for shielding the hands must be rendered biologically sterile but should not block the image field that is currently viewed on the fluoroscope. Because the shielding material becomes biologically contaminated with blood and other body fluids it is preferable that it is disposable or is enclosed in a disposable sterile sheath. If disposable the shielding material should not contain toxic metals like lead which would contaminate the waste stream.

There are two existing products that are designed to shield the hands, both meet the needs to some respect but both have significant drawbacks. Product 1 consists of a flexible sterile glove made of an elastomer that incorporates one or more heavy metal attenuating powders in the elastomer matrix. Product 2 consists of a flexible pad made from an elastomer charged with one or more heavy metal attenuating powders in the elastomer matrix, and covered with a sterile over-layer. The gloves are designed to replace the standard thin latex surgeon's gloves that are employed in all surgical operations but adding a shielding component. The main drawback for these gloves is that there is a tradeoff between a thin flexible material that easily permits manipulation of thin catheters and other instruments and the degree of protection provided by the material. Disposable single-use gloves that are sufficiently flexible typically provide less than 50% attenuation. The high cost relative to its low level of shielding effectiveness makes this product a poor choice. The sterile flexible pads of product 2 (see for example U.S. Pat. No. 4,938,233) are far more effective in providing shielding of the hands, The pad is placed directly on the patient's body directly over the catheter access site with a cut-out to provide access. The flexible shield is constructed to have sufficient attenuation to reduce the radiation exposure to the hands by 75% or more. Because the pads can be relatively large, they can shield a greater region of the fluoroscopist's body than just the hands. These pads however have two significant drawbacks. The first drawback is that the pads are relatively heavy and when positioned correctly on the patient, they hang over the side of the patient's body facing the fluoroscopist. To keep them in place the pads have an adhesive tape backing that sticks to the large loose sterile drape that covers the patient's body. This position hanging off the side the patient however makes the drape susceptible to sliding to the floor taking the sterile drape and all the instruments with it. If this should occur the patient must be re-draped and all the sterile instruments must be replaced. Potentially this problem could be addressed by a fixture or method that attaches drapes to the patient; however there is a more serious drawback. The second drawback is that the shielding material, while reducing radiation exposure to the fluoroscopist and staff can significantly increase the exposure to the patient in ways that would not be obvious to the clinical staff. The problem relates to the function of the automatic exposure control (AEC) system used in virtually all fluoroscopes. The AEC system automatically adjusts the x-ray machine exposure rate to compensate for variations in the attenuation in the patient to ensure that fluoroscopic image quality remains constant regardless of the body thickness or density. Normal fluoroscope operation configures the x-ray source below the patient with the image receptor above. Pad type shielding materials are placed on the upper surface so that if the fluoroscopist moves the fluoroscope so that the beam encounters the shield, the automatic exposure control will increase the exposure rate sufficiently to penetrate through the shield. This substantial increase in exposure rate is received by the patient and is greatest at the skin surface where the x-ray beam enters; this is not in the best interest of the patient. The purpose of the invention is to provide a shield that is more effective than the gloves and at least as effective as the pad type devices but without the drawbacks of potentially sliding off the patient or substantially increasing the patient radiation dose.

SUMMARY OF THE INVENTION

It is an object of this invention to place a shielding barrier between the tissues of the patient that are in the field of the direct x-ray beam and from which the scattered radiation is emitted, and the location of the physician's hands at the catheter insertion point. The present invention meets the object without the drawbacks of the prior art. The present invention comprises a flexible shield, preferably formed from a flexible elastomeric fabric, charged with one or more attenuating, non-toxic heavy metals and supported and aligned by a simple metal or plastic frame that holds the shield so that it drapes downward from the frame located vertically above the patient. The shield drape is located so as to place it between the scatter producing tissues and the position of the fluoroscopist's hands while controlling and manipulating the catheter and instruments installed within the catheter.

BRIEF DESCRIPTION OF THE SEVERAL VIEWS OF THE DRAWINGS

FIG. 4 is a view of the support frame for the hand shield of the present invention;

DETAILED DESCRIPTION OF THE INVENTION

Figure 1:
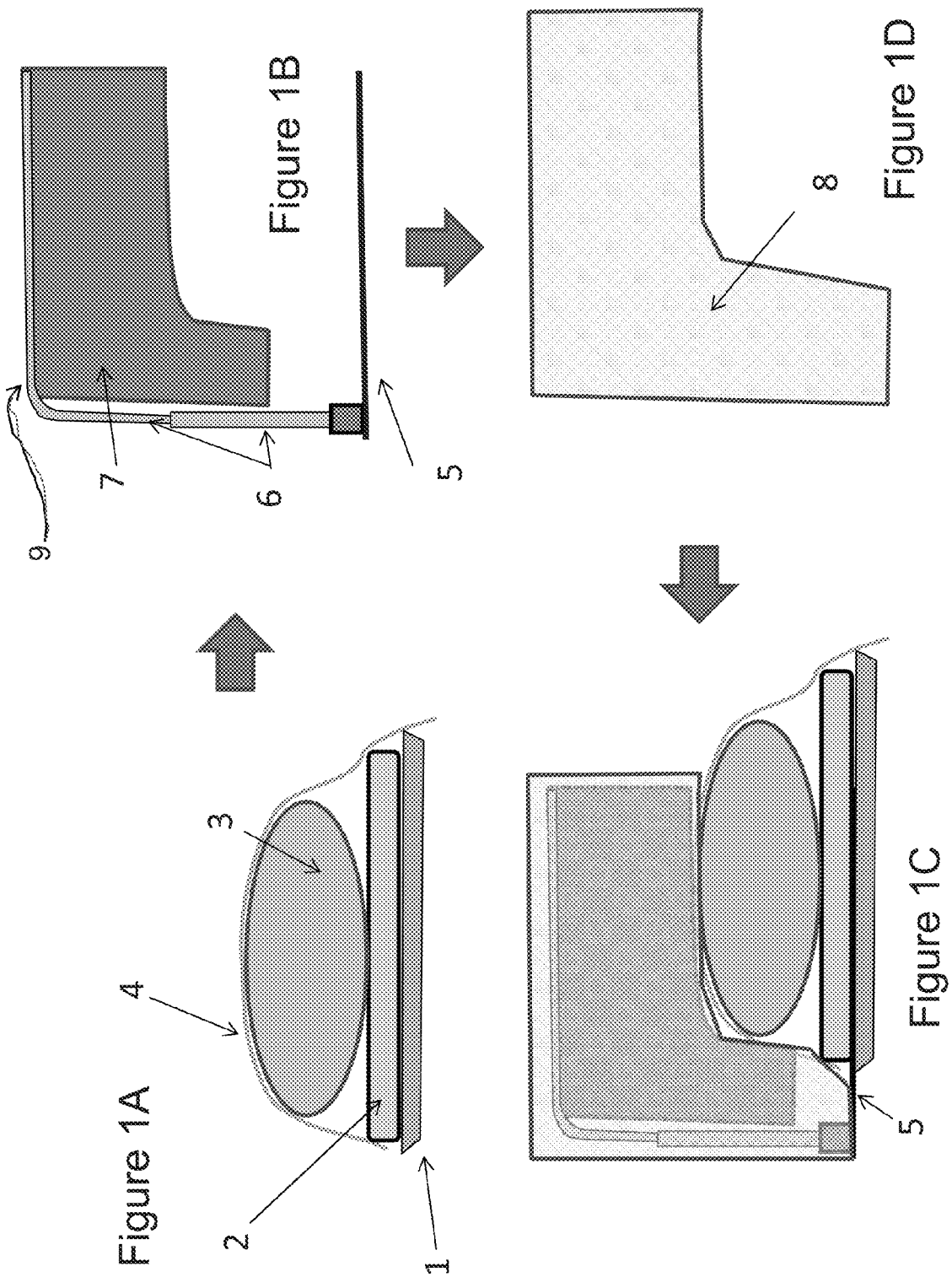
FIGS. 1A, B, C and D schematically illustrate the patient and supporting table in cross section, plus the sterile draping and alignment of the transverse shield of the present invention.

Referring to the drawings in FIGS. 1A, B, C and D, the patient 3 is supported on a foam filled mattress 2 over the cantilever support table 1, and a sterile drape 4 is placed over the surface of the patient. The invention consists of a 2-3 mm thick x-ray transparent carbon fiber (or other rigid plastic) plate 5 supporting a vertically telescoping strut 6 that supports the weight of an x-ray attenuating flexible fabric shield 7 that is formed to conform to the surface of the patient 3. To render the assembly sterile, the assembly is inserted within a fitted disposable drape 8, before inserting the rigid support plate 5 between the patient support table 2 and the foam filled mattress 3, with the weight of the patient 4 (shown in cross-section as a simple ovoidal shape) on the mattress keeping the plate 1 in place. The shield 7 may comprise a flexible sheet of polymer loaded with radiation-attenuating heavy metal particles covered by a removable disposable sterile cover. In this way sterility of the field is maintained without having to dispose of the potentially toxic heavy metal-loaded vertical shield 7.

Figure 6:
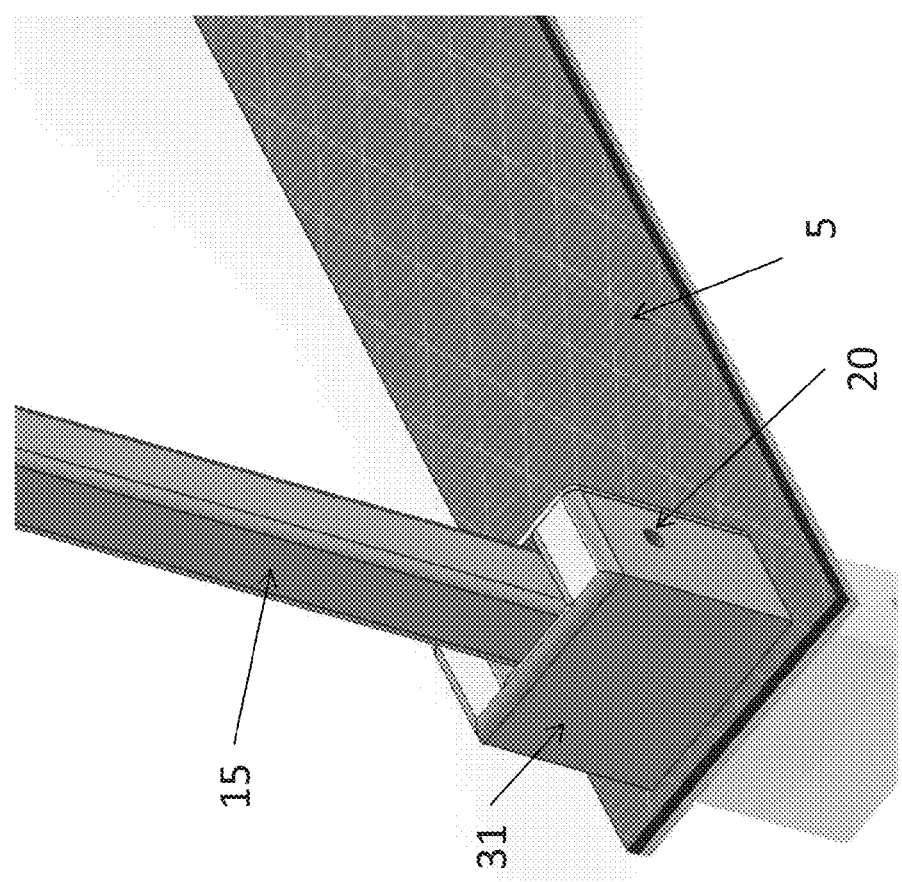
FIG. 6 a magnified view of the telescoping mechanism that permits vertical adjustment of the present invention.

A preferred embodiment of the shield frame is shown in FIG. 4. The base support 5 that is inserted between the patient supporting table and the foam filled mattress is constructed of a rigid but x-ray transparent 2-4 mm thick plate of carbon fiber reinforced polymer. An anodized aluminum block bracket 14 shown magnified in FIG. 6 is attached to one end of the base support 5. The bracket 14 is machined to accept a hollow vertical tube 15 with a square or rectangular cross-section. The hollow tube 15 is preferentially constructed of stainless steel, to achieve the long-lasting durability desired, because it is a material inert to body secretions and 31 other corrosive materials.

Figure 5:
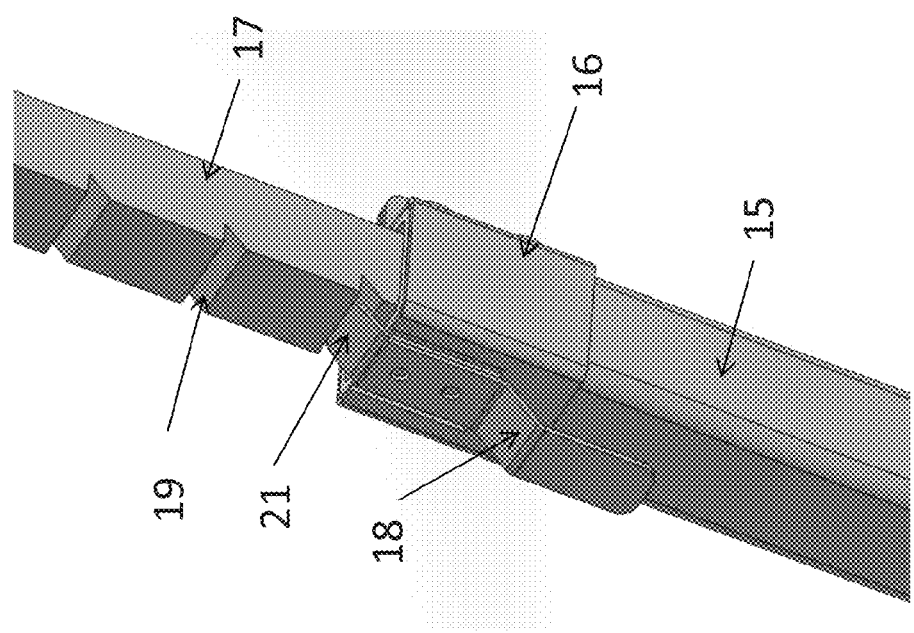
FIG. 5 is magnified view of the base clamp.

A spring loaded pin 21, located in the base, nests in a recess 19 in the hollow tube 15 to hold the tube 15 in position. Referring again to FIG. 4 a solid stainless steel rod 17 with a square cross-section a 90° radiused bend to nest at one end in the hollow vertical tube 15 and to support the weight of the radiation shield (not shown). Shown in magnified view in FIG. 5 an adjustment mechanism 16 is located at the upper end of the hollow tube 15 to permit alteration of the vertical height of the horizontal portion of steel rod 17 and thus the shield that it supports above patients of differing thickness. The adjustment mechanism incorporates a tensioning spring tab that is user actuated by lever 18 to move tab 21 from its position that intersects grooved slots 19 in rod 17. Tab 21 is thus spring loaded to intersect grooved slots 19 and thus holding rod 17 and the shield that it supports at a particular elevation so that its bottom margin conforms to the upper surface of patients of varying thickness and shapes, but permits extraction of the rod 17 by pulling upward by the user. Squeezing of lever 18 against tube 15, thus permits the weight of rod 17 and the shield it support to telescope into tube 15 moving the shield downward. The shield is adjusted upward by merely pulling upward on rod 17 with or without squeezing release lever 18. Note that the vertical portion of rod 17 is of sufficient length and there are sufficient grooved slots 19 in rod 17 to permit vertical adjustment over a distance of at least 12 inches (305 mm).

Figure 2:
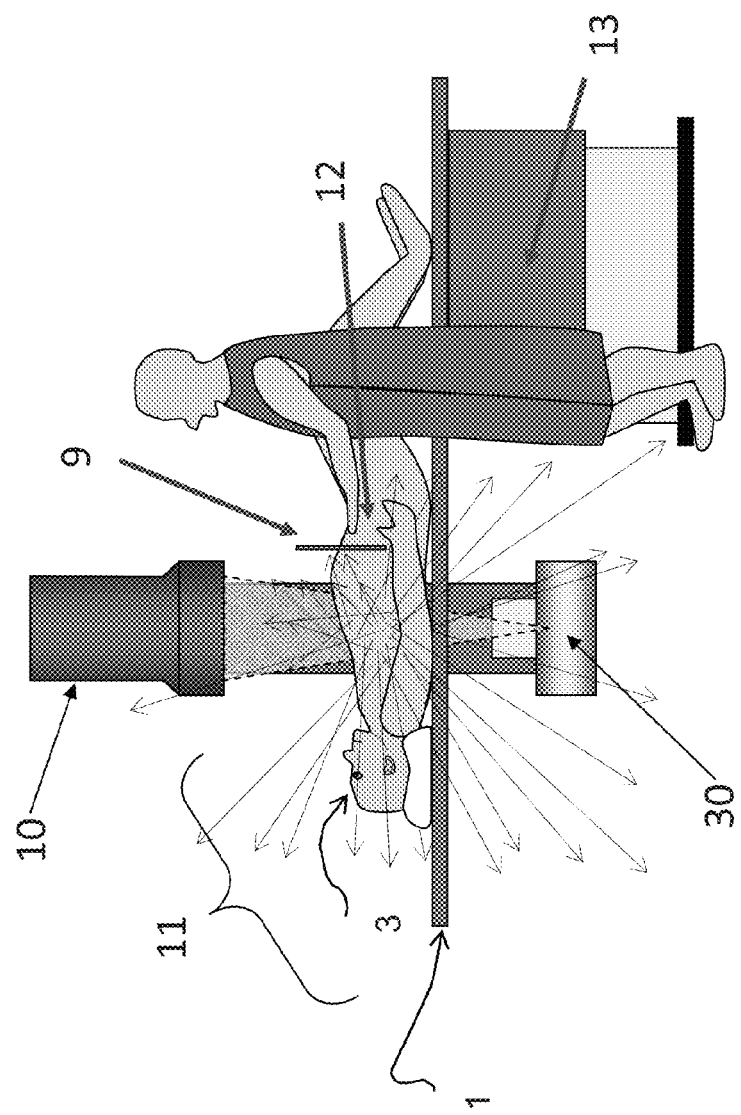
FIG. 2 shows the patient, fluoroscope and operating physician from a side elevation view.

The bottom edge of the flexible vertical shield drape 9, as shown in FIGS. 2 and 6, is cut in an arcuate shape to more easily conform to the general shape of a patient's body, shown diagrammatically as the simple ovoidal shape 3.

As illustrated in FIG. 2, the patient is supported on a cantilever table 13 with vertical adjustment capability so that the patient can be positioned between the x-ray source and image receptor of the articulated fluoroscope 10. The scattered radiation 11 presenting the hazard to the physician and other staff is emitted from the tissue volume of the patient that is within the direct x-ray beam outlined with dotted lines. The flexible, preferably elastomeric, vertical shield 9 is oriented to extend vertically above the patient's surface to provide a protected region 12 around the skin surface, e.g., at the groin of the patient where the catheter is inserted into an artery or vein and is manipulated. For clarity, the supporting frame, clamp and mounting plate for the apparatus are not shown in FIG. 2.

Figure 3:
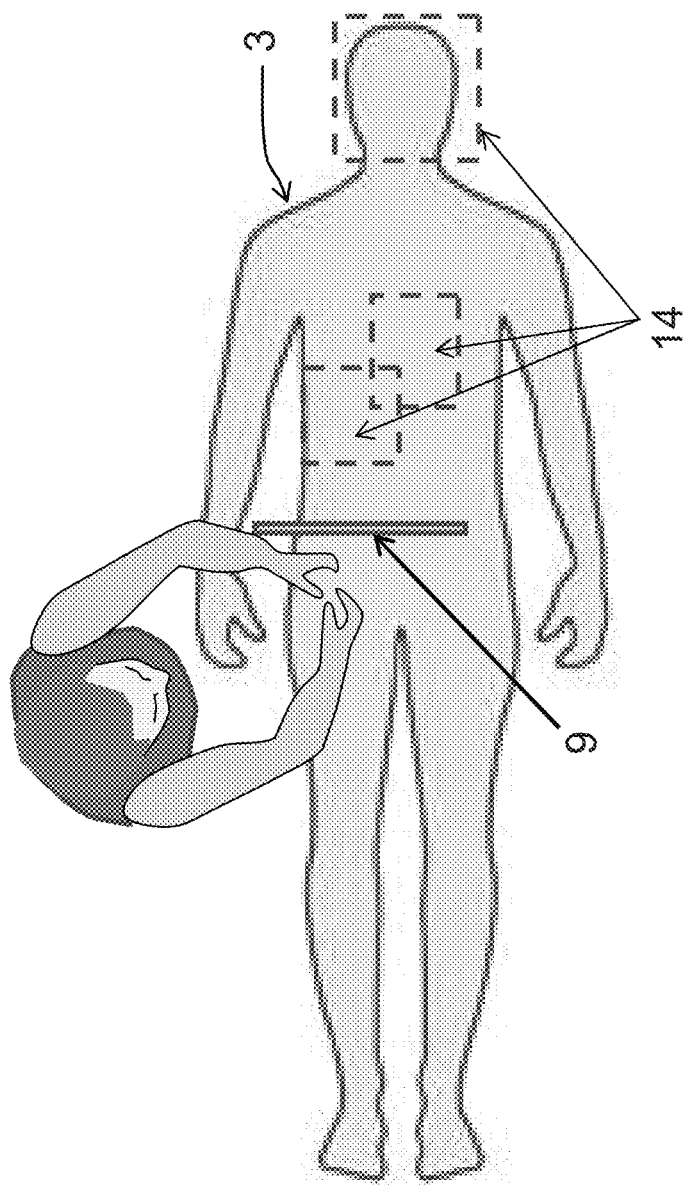
FIG. 3 is a top plan view of the system shown in FIG. 2.

The configuration of use of the apparatus is also shown in FIG. 3 viewed from above looking down on the patient and the physician; the supporting frame for the shield is not shown. The physician's hands are located behind the barrier 9 and separated from the typical locations of the x-ray beam on the patient 14 (as shown by the scattering arrows).

The shielding drape 9 supported by the frame may also come in several sizes, if desired. It is preferred that regardless of the length of the drape 9, the lower edge has an arcuate shape to accommodate the different sized individual patients. As shown in FIG. 2, the surgeon can keep his hands below the top of the vertical drape shield 9, and they are thus protected from almost all of the scattered radiation. The drape 9 should, of course, be placed between the location of the x-ray beam, on the body of the patient, and the entry point of the catheter. For a groin access catheterization procedure this would be usually located just below the waist.

Other embodiments and Examples of the invention will be apparent to those skilled in the art from a consideration of the specification or practice of the invention disclosed herein, and the scope of this invention is determined by the following claims herewith.

What is claimed is:

1. An assembly, comprising:
   a medical operating surface, having a length and a width, the length being greater than the width;
   a flexible polymer sheet, incorporating radiation-attenuating heavy metal powder;
   a frame connected to and supporting the polymer sheet in an extended position in two dimensions, extending across the width of the medical operating surface;
   a bracket connected to the frame for supporting the frame and the polymer sheet in a vertical orientation above the medical operating surface;
   a clamp being secured to the operating surface and secured to the bracket, for holding up the bracket in a position to support the frame and the polymer sheet in a vertical orientation extending across the medical operating surface;
   a fluoroscope for projecting focused high energy radiation at a patient supported on the medical operating surface, the focused high energy radiation being focused on a location at one end of the medical operating surface, intended to provide fluoroscopic guidance for a surgeon located at a position along the length of the medical operating surface distal from the focused location of the focused high energy radiation, the medical procedure involving the use of remotely controlled instruments by a surgeon;

the clamp and bracket supporting the frame so as to extend across the medical operating surface in a direction substantially transverse to the long dimension of the medical operating surface at a position along the length of the operating medical surface to be located intermediate the location of the hands of the surgeon operating with the remotely controlled instruments and the location of the actual medical procedure;

the polymer sheet extending vertically to a level such that the heavy metal powders serve to attenuate the high energy radiation directed to the operating location by the fluoroscope, so as to protect the hands of the medical operator manipulating the catheter at the distal location.

2. The assembly of claim 1 wherein the flexible polymer sheet is formed of an elastomer and incorporates metal powders selected from the group consisting of zinc, tin, antimony, tungsten, tantalum, and bismuth or powders formed from nontoxic compounds of such metals.

3. The assembly of claim 1 where the flexible elastomer sheet incorporates a salt of barium selected from the group consisting of barium sulfate and barium carbonate and combinations thereof, in combination with a metal powder selected from the group consisting of zinc, tin, antimony, tungsten, tantalum, and bismuth or powders formed from nontoxic compounds of such metals.

4. The assembly of claim 1 wherein the polymer sheet and frame are encased in a removable, disposable sterile cover.

5. The assembly of claim 1 wherein the vertically lowest edge of the polymer sheet extending across the operating surface is formed so as to conform to the surface of the body of a patient supported on the medical operating surface.

6. The assembly of claim 1 further comprising a mattress on the medical operating surface for directly supporting a patient, and a rigid, x-ray-transparent plate provided between the medical operating surface and the mattress, to provide a rigid attachment plate for the clamp.

7. The assembly of claim 1 wherein the polymer sheet is formed of overlapping vertical strips extending along the frame, to assist in conforming to any irregular shape of a patient's body surface.

8. The assembly of claim 1 wherein the frame is vertically adjustable to raise and lower the vertical height of the shield for use with patients of different body thicknesses with resulting variation in the height of the body surface above the medical operating surface.

9. A method for protecting the hands of a surgeon operating remotely on a patient with a catheter inserted medical device, inserted at a location distal from the location of the operation, wherein the operation is viewed via a fluoroscope involving the use of high energy radiation focused on the location of the operation, where the patient is supported on a medical operating surface, the method comprising:

providing a vertically oriented radiation shield, extending upwardly from and across the body of the patient, along a line between the location of the surgeon and the location of the operation subject to the high energy focused radiation, the radiation shield comprising a radiation-attenuating, heavy metal-filled, flexible polymer sheet extending vertically above and across the body of the patient to protect the hands of the surgeon from the high energy radiation from the fluoroscope procedure; the flexible polymer sheet being supported on a frame, which in turn is rigidly connected to a clamp, for removably holding the frame in a vertical position extending across and above the body of the patient, at a position intermediate the catheter insertion location and the location of the operation.

* * * * *